(12) United States Patent
Davies et al.

(10) Patent No.: US 9,958,398 B2
(45) Date of Patent: May 1, 2018

(54) MEASURING PARAMETERS OF A CUT GEMSTONE

(71) Applicant: De Beers UK Ltd., London (GB)

(72) Inventors: Nicholas Matthew Davies, Berkshire (GB); Siobhan D'Gama, London (GB); Peter Stanley Rose, Buckinghamshire (GB); Maxwell Ralph Willis, Oxfordshire (GB)

(73) Assignee: De Beers UK Ltd., London (GB)

( * ) Notice: Subject to any disclaimer, the term of this patent is extended or adjusted under 35 U.S.C. 154(b) by 83 days.

(21) Appl. No.: 14/905,318

(22) PCT Filed: Jul. 17, 2014

(86) PCT No.: PCT/EP2014/065454
§ 371 (c)(1),
(2) Date: Jan. 15, 2016

(87) PCT Pub. No.: WO2015/007873
PCT Pub. Date: Jan. 22, 2015

(65) Prior Publication Data
US 2016/0178530 A1 Jun. 23, 2016

(30) Foreign Application Priority Data
Jul. 18, 2013 (GB) .................................. 1312888.9

(51) Int. Cl.
*G01N 21/00* (2006.01)
*G01N 21/87* (2006.01)
(Continued)

(52) U.S. Cl.
CPC ............. *G01N 21/87* (2013.01); *B07C 5/342* (2013.01); *G01N 21/39* (2013.01); *G01N 21/64* (2013.01);
(Continued)

(58) Field of Classification Search
CPC ........ G01N 21/87; G01N 21/39; G01N 21/64; G01N 21/65; B07C 5/342
See application file for complete search history.

(56) References Cited

U.S. PATENT DOCUMENTS 5,386,295 A * 1/1995 Switalski .................. G01J 3/02
250/458.1
6,167,290 A * 12/2000 Yang .................... A61B 5/1455
600/316
(Continued)

FOREIGN PATENT DOCUMENTS

CH 700 695 A2 9/2010
GB 2 274 165 A 7/1994
(Continued)

OTHER PUBLICATIONS

International Search Report and Written Opinion for corresponding International Application No. PCT/EP2014/065454 dated Oct. 10, 2014.
(Continued)

*Primary Examiner* — Abdullahi Nur
(74) *Attorney, Agent, or Firm* — Renner, Otto, Boisselle & Sklar, LLP

(57) ABSTRACT

Apparatus and corresponding methods for measuring a plurality of parameters of a cut gemstone while it is positioned at a single measurement location. Apparatus comprise a plurality of light sources, each configured to emit light at a different one of a plurality of emission wavelengths or ranges of wavelengths such that the emitted light illuminates at least part of the measurement location. Apparatus further comprise a sensor assembly configured to sense light at a plurality of sensing wavelengths or ranges of wavelengths for measuring the plurality of parameters. The sensed light is received at the sensor assembly from the measurement location as a result of illumination of a cut gemstone located at the measurement location.

37 Claims, 8 Drawing Sheets

(51) Int. Cl.
    *B07C 5/342*    (2006.01)
    *G01N 21/39*    (2006.01)
    *G01N 21/64*    (2006.01)
    *G01N 21/65*    (2006.01)
(52) U.S. Cl.
    CPC ....... *G01N 21/65* (2013.01); *G01N 2201/068* (2013.01); *G01N 2201/06113* (2013.01); *G01N 2201/08* (2013.01)

(56) References Cited

U.S. PATENT DOCUMENTS

| | | | |
|---|---|---|---|
| 6,980,283 B1 | 12/2005 | Aggarwal | |
| 2009/0182520 A1* | 7/2009 | Luxembourg | ....... G01N 33/381 |
| | | | 702/81 |
| 2010/0185067 A1* | 7/2010 | Gupta | .................. A61B 5/0097 |
| | | | 600/323 |

FOREIGN PATENT DOCUMENTS

| | | |
|---|---|---|
| GB | 2 295 227 A | 5/1996 |
| WO | WO 88/05534 A1 | 7/1988 |
| WO | WO 02/06797 A1 | 1/2002 |

OTHER PUBLICATIONS

British Search Report dated Jan. 14, 2014 for corresponding British Application No. GB1312888.9.

\* cited by examiner

MEASURING PARAMETERS OF A CUT GEMSTONE

TECHNICAL FIELD

The invention relates to, but is not limited to, methods and apparatus for measuring parameters of a cut gemstone. The methods and apparatus may measure parameters of cut gemstones for sorting the cut gemstones.

BACKGROUND

In order to maintain consumer confidence that diamond products are properly disclosed, it is important that the diamond industry has practical methods for testing cut gemstones to determine whether they are natural diamonds, synthetic diamonds or simulants. Similarly it is important that it has methods for determining whether a diamond has been artificially treated, for example to change its colour.

Apparatus exist that are capable of distinguishing diamond gemstones from simulants, and for measuring a parameter of a diamond to give an indication of whether the diamond is likely to be natural or synthetic, or whether it has been treated, for example to improve its colour. Typically, such apparatus perform a measurement, then place diamonds in respective bins dependent on the result of the measurement. However, such apparatus are often unreliable and further tests and/or measurements are often required to confirm whether or not a gemstone is a diamond and, if so, whether it is natural or synthetic and/or has been treated.

Additionally, the determination of other physical parameters of a gemstone, such as colour, size and cut, is an important process in the diamond industry.

SUMMARY

According to the invention in a first aspect, there is provided an apparatus for measuring a plurality of parameters of a cut gemstone while it is positioned at a single measurement location, the apparatus comprising: a plurality of light sources each configured to emit light at a different one of a plurality of emission wavelengths or ranges of wavelengths such that the emitted light illuminates at least part of the measurement location; and a sensor assembly configured to sense light at a plurality of sensing wavelengths or ranges of wavelengths for measuring the plurality of parameters, the sensed light being received at the sensor assembly from the measurement location as a result of illumination of a cut gemstone located at the measurement location.

Optionally, the apparatus further comprises a support assembly for retaining the cut gemstone at the measurement location to facilitate the transmission of light in and out of a facet of the cut gemstone.

Optionally, the plurality of light sources comprises a broadband light source configured to emit light for measuring the absorption of a cut gemstone.

Optionally, the broadband light source is configured to emit light at wavelengths in the range from about 300 nm to about 520 nm.

Optionally, the plurality of light sources comprises one or more laser light sources.

Optionally, the one or more laser light sources comprises a laser light source configured to emit light at a wavelength suitable for stimulating Raman emission spectrum at a detectable wavelength from a cut gemstone.

Optionally, the laser light source is configured to emit light at about 660 nm.

Optionally, the one or more laser light sources comprises at least one laser light source configured to emit light at a wavelength suitable for stimulating photoluminescence in a cut gemstone.

Optionally, the at least one laser light source configured to emit light at a wavelength for stimulating photoluminescence in a cut gemstone comprises at least one laser light source configured to emit light substantially at a wavelength of one of about 325 nm, about 375 nm, about 458 nm, about 514 nm, about 785 nm and about 830 nm.

Optionally, the plurality of light sources comprises a UV light source.

Optionally, the sensor assembly comprises a spectrometer comprising a wavelength restriction means configured to prevent detection of light in a certain wavelength range.

Optionally, the spectrometer comprises a charge coupled device and wherein the wavelength restriction means comprises a mask located before the charge coupled device on a path of light entering the spectrometer.

Optionally, the spectrometer further comprises a diffraction grating located before the mask on the path of light entering the spectrometer.

Optionally, the wavelength range is from 350 nm to 400 nm.

Optionally, the apparatus further comprises a broad band light source configured to emit light for measuring absorption of a cut gemstone, wherein the UV light source is configured to emit light for measuring fluoresence of a cut gemstone, and wherein the spectrometer is configured to measure fluorescence in a wavelength range from 400 nm to 508 nm and to measure absorption in two ranges from 300 nm to 350 nm and from 400 nm to 508 nm.

Optionally, the apparatus is configured to measure fluorescence and absorption of a cut gemstone simultaneously.

Optionally, the sensor assembly comprises a plurality of sensors, each configured to sense light at a different one or more of the plurality of sensing wavelengths or ranges of wavelengths.

Optionally, the plurality of sensors comprises a spectrometer configured to sense light at a range of wavelengths for measuring the absorption of a cut gemstone.

Optionally, the spectrometer is configured to sense light at a wavelength range from about 300 nm to about 520 nm.

Optionally, the plurality of sensors comprises a spectrometer configured to sense light at a range of wavelengths for measuring the Raman emission spectrum of a cut gemstone.

Optionally, the spectrometer is configured to sense light at a wavelength range from 700 nm to 800 nm.

Optionally, the plurality of sensors comprises at least one spectrometer configured to sense light at a wavelength for measuring the photoluminescence of a cut gemstone.

Optionally, the at least one spectrometer is configured to sense light at a wavelength in at least one of a range from about 380 nm to about 520 nm; and a range from about 460 nm to about 850 nm.

Optionally, the plurality of sensors comprises an image capturing device configured to sense light at a wavelength for measuring the fluorescence or phosphorescence of a cut gemstone.

Optionally, the image capturing device is a camera configured to sense light at a wavelength range from about 400 nm to about 700 nm.

Optionally, the image capturing device is configured to capture an image for determining the cut of a gemstone and/or the size of a gemstone.

Optionally, the apparatus further comprises a means for directing light emitted from the light source assembly to the measurement location.

Optionally, the means for directing light from the light source assembly to the measurement location comprises an optical fibre.

Optionally, the apparatus further comprises a means for directing light from the measurement location to the sensor assembly.

Optionally, the means for directing light from the measurement location to the sensor assembly comprises an optical fibre.

Optionally, the apparatus further comprises a multi-furcated optical fibre assembly configured to direct light from the light source assembly to the measurement location and to direct light from the measurement location to the sensor assembly.

Optionally, the multi-furcated optical fibre assembly comprises a plurality of optical fibre filaments, each configured to direct light from one of the plurality of light sources or to one of the plurality of sensors.

Optionally, the means for directing light emitted from the light source assembly to the measurement location comprises an optical multiplexer comprising a plurality of inputs each connected to a different one of the plurality of light sources, and an output for directing light to the measurement location, the optical multiplexer configured to select light received at one of the plurality of inputs and allow the selected light to be emitted from the output.

Optionally, the means for directing light from the measurement location to the sensor assembly comprises an optical demultiplexer comprising an input configured to receive light from the measurement location, and a plurality of outputs each connected one of the plurality of sensors, the optical demultiplexer configured to select one of the plurality of outputs and to allow light received at the input to be emitted from the selected output.

Optionally, the optical multiplexer and the optical demultiplexer form an optical multiplexer/demultiplexer.

Optionally, the apparatus further comprises means for determining whether a cut gemstone is natural or synthetic based on the measured parameters.

Optionally, the apparatus further comprises a means of distinguishing between diamond and simulant.

Optionally, the apparatus further comprises means for determining whether a cut gemstone has been treated in order to improve its colour based on the measured parameters.

Optionally, the apparatus is configured to measure simultaneously the absorption of a cut gemstone and the Raman emission spectrum of a cut gemstone.

Optionally, the apparatus is configured to measure simultaneously the photoluminescence of a cut gemstone and the Raman emission spectrum of a cut gemstone.

Optionally, the apparatus is configured to measure simultaneously the absorption of a cut gemstone and the photoluminescence of a cut gemstone.

Optionally, the cut gemstone is diamond.

According to the invention in a second aspect, there is provided a sorting apparatus comprising any apparatus described above and configured to sort cut gemstones in dependence on the measured parameters.

Optionally, sorting the cut gemstones comprises identifying whether the gemstone has been treated to improve its colour.

Optionally, sorting the cut gemstones comprises determining one or more of the colour, size and cut of the gemstone.

Optionally, sorting the cut gemstones comprises distinguishing between diamonds and simulants.

According to the invention in a third aspect, there is provided a method for measuring a plurality of parameters of a cut gemstone while it is positioned at a single measurement location, the method comprising: operating a first light source to illuminate at least part of the cut gemstone with light having a first emission wavelength or range of wavelengths; sensing light received from the measurement location at a first sensing wavelength or range of wavelengths as a result of illumination of the cut gemstone at the first emission wavelength or range of wavelengths; measuring a first parameter of the cut gemstone based on the sensed light at the first sensing wavelength or range of wavelengths; operating a second light source to illuminate at least part of the cut gemstone with light having a second emission wavelength or range of wavelengths different to the first emission wavelength or range of wavelengths; sensing light received from the measurement location at a second sensing wavelength or range of wavelengths as a result of illumination of the cut gemstone at the second emission wavelength or range of wavelengths; and measuring a second parameter of the cut gemstone based on the sensed light at the second sensing wavelength or range of wavelengths.

Optionally, the first sensing wavelength or range of wavelengths is different to the second sensing wavelength or range of wavelengths.

Optionally, each of the first and second light sources is operated such that they emit light simultaneously.

According to the invention in a fourth aspect, there is provided a method for sorting cut gemstones comprising any method described above and further comprising sorting the cut gemstones in dependence on the measured parameters.

Optionally, sorting the cut gemstones comprises identifying whether the gemstones have been treated to improve their colour.

Optionally, sorting the cut gemstones comprises identifying whether the gemstones are diamond or simulant.

According to the invention in a fifth aspect, there is provided a non-transitory computer program product configured to carry out any method described above.

BRIEF DESCRIPTION OF THE DRAWINGS

Exemplary embodiments of the invention are described herein with reference to the accompanying drawings, in which.

DESCRIPTION

Generally, disclosed herein are methods and apparatus for measuring a plurality of parameters of a cut gemstone. In particular, disclosed herein are methods and apparatus for measuring a plurality of parameters of a cut gemstone while the gemstone is at a single measurement location.

As used herein, the term "parameter" in respect of a cut gemstones encompasses the absorption of a gemstone, the Raman and or photoluminescence spectra of a gemstone, the colour or clarity of a gemstone, the size of a gemstone and the cut of a gemstone.

The inventors have appreciated that the reliability and, in particular, the speed with which a cut gemstone is sorted can be improved if a plurality of measurements is undertaken by a single apparatus at a single measurement location.

In particular exemplary methods and apparatus, an absorption measurement and a Raman or photoluminescence measurement may each be undertaken while a cut gemstone is at a single measurement location. Those two measurements have previously not been typically performed by a single apparatus, but with two individual instruments.

Instruments are available to assist in identification of natural untreated diamonds, synthetic diamond and treated diamonds. For example, DiamondSure®, DiamondView® and DiamondPLus® are manufactured by the Diamond Trading Company and are used by grading laboratories. DiamondSure® operates by measuring the absorption of visible light by a diamond. Those stones having an absorption spectrum indicating potential synthetics or treated diamond (limited to diamond types IaB or IIa) are categorised as such. Stones referred by DiamondSure® are tested using DiamondView® and are illuminated with ultraviolet radiation. A user can study images of the resulting surface fluorescence, captured using a camera. Given that the fluorescence colours and patterns from synthetic diamond differ greatly from those of natural diamonds, DiamondView® makes it possible for gemmological laboratories and jewellery professionals to determine whether a diamond is natural or synthetic. Phosphorescence images, captured using DiamondView® can provide additional evidence.

1-2% of diamonds with natural origin are nominally free of nitrogen impurity. These are called type II diamonds and they form an important category of DiamondSure® referrals to DiamondView®. After the natural origin has been confirmed using DiamondView®, it is necessary to check whether such stones have been artificially treated to improve their colour. The stones are tested using DiamondPLus, which can be used to make a rapid photoluminescence measurement that significantly reduces the number of type II diamonds that need further, more detailed testing.

Figure 1A:
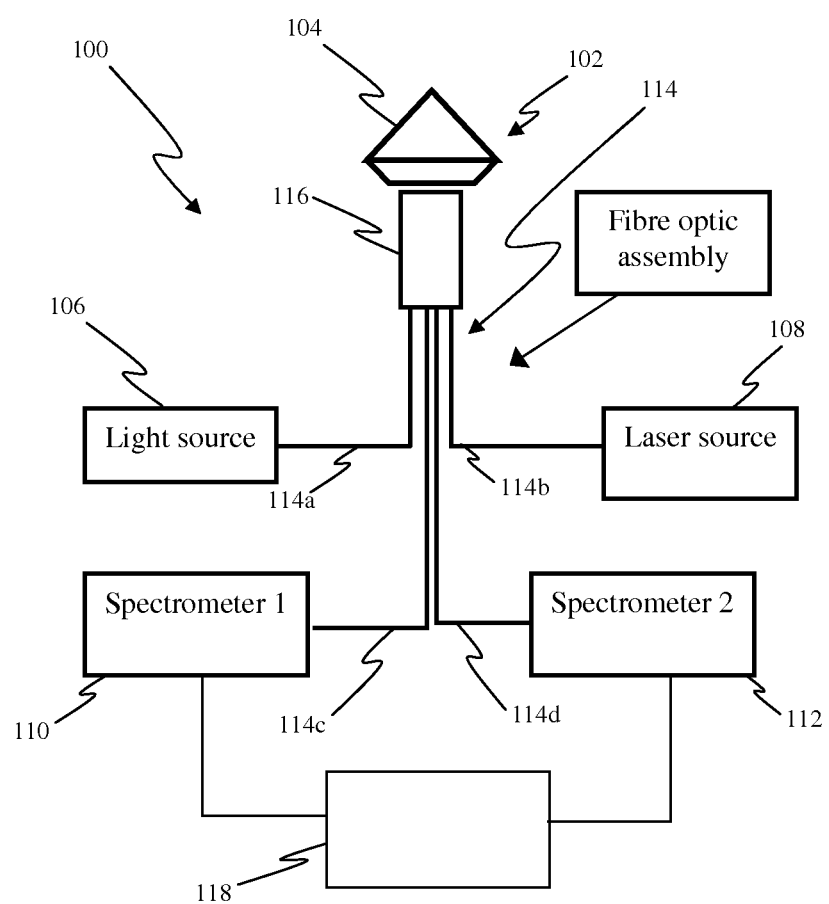
FIG. 1a shows a schematic representation of an apparatus for measuring a plurality of parameters of a cut gemstone.

FIG. 1a shows a schematic representation of an apparatus for measuring a plurality of parameters of a cut gemstone while it is positioned at a single measurement location. The apparatus 100 defines a measurement location 102, at which a cut gemstone 104 is positioned.

In specific exemplary apparatus and methods, the cut gemstone 104 is a diamond.

The measurement location 102 may comprise a flat surface on which a cut gemstone can be positioned manually, e.g. by a technician. In other exemplary apparatus, the measurement location 102 may be coincident with a path of a transportation means, e.g. a conveyer or vacuum transport. In such apparatus, the conveyor may be configured to transport the cut gemstone 104 from a first location, e.g. a hopper, to the measurement location 102. In other exemplary apparatus, the measurement location may be located in a receptacle for holding cryogenic fluid, such as liquid nitrogen. In such apparatus, cut gemstones may be submerged in liquid nitrogen while one or more measurements are carried out. Gemstones may be placed in a cryostat with a window through which light may pass.

While the cut gemstone 104 is positioned at the measurement location 102, a plurality of parameters of the gemstone 104 are measured. In the exemplary apparatus of FIG. 1a, a first light source 106 is configured to emit light at a first emission wavelength or range of wavelengths. In the exemplary apparatus 100 of FIG. 1a, the first light source 106 is a broadband light source, for example, a tungsten halogen lamp. In the example shown in FIG. 1a the first light source 106 is configured to emit light at a spectrum from 300 nm to 520 nm wavelengths.

As used herein, the term "broadband light source" encompasses light sources that emit light across a range of wavelengths simultaneously. Broadband light sources also encompass light sources that do not emit light at a specific wavelength with a coherent phase, e.g. a single frequency laser. A broadband light source may, for example, be a lamp or LED.

A second light source 108 is configured to emit light at a second emission wavelength or range of wavelengths. In the exemplary apparatus 100 of FIG. 1a, the second light source 108 is a laser light source configured to emit light at a wavelength of 660 nm.

The apparatus 100 is for measuring absorption at one wavelength range, for example 300 nm to 520 nm, and for measuring Raman scattering and or photoluminescence at another wavelength range, for example 700 nm to 800 nm. The Raman scattering and or photoluminescence may be stimulated by a 660 nm laser source.

Accordingly, a first sensor 110 is configured to sense light at a first sensing wavelength or range of wavelengths. In the exemplary apparatus 100 of FIG. 1a, the first sensor 110 is a spectrometer configured to sense light of a wavelength in the range from 300 nm to 520 nm.

A second sensor 112 is configured to sense light at a second sensing wavelength or range of wavelengths. In the exemplary apparatus 100 of FIG. 1a, the second sensor is a spectrometer configured to sense light of a wavelength in the range from 700 nm to 800 nm.

The first and second light sources 106, 108 and the first and second sensors 110, 112 are each optically coupled to a fibre optic assembly 114. The fibre optic assembly 114 is configured to direct light from the first and second light sources 106, 108 to the measurement location 102. Further, the fibre optic assembly 114 is configured to direct light from the measurement location 102 to the first and second sensors 110, 112.

The fibre optic assembly 114 is a multi-furcated fibre optic comprising four fibre optic filaments 114a-d. The fibre optic filaments 114a-d are held together in a single fibre optic cable 116. The fibre optic cable 116 is arranged such that an end of the filaments 114a-d is each directed to the measurement location 102. The fibre optic assembly 114 comprises four flying leads, one for each filament, which may be optically coupled to a light source 106, 108 or a sensor 110, 112. The fibre optic assembly 114 is configured to couple light directly to, and detect light directly from, the gemstone 104 when positioned at the measurement location 102. In order to aid this, the fibre optic filaments 114a-d are well polished and are in intimate contact with a table facet of the gemstone 104. The gemstone 104 may be polished.

The first light source 106 is connected to the filament 114a, which directs light emitted by the first light source 106 to the measurement location 102 such that it illuminates at least a part of the measurement location 102. The second light source 108 is connected to the filament 114b, which directs light emitted by the first light source 108 to the measurement location 102 such that it illuminates at least a part of the measurement location 102. The first sensor 110 is connected to the filament 114c, which directs light from the measurement location 102 to the first sensor 110.

The exemplary apparatus 100 of FIG. 1a comprises a processor 118 in electrical communication with each of the first and second sensors 110, 112. The processor 118 is configured to determine whether the gemstone is natural, synthetic or treated based on measurements obtained by the sensors 110, 112. The processor 118 is an optional feature. In this configuration the processor could be configured to output a colour grade or category from, for example, an absorption measurement.

In exemplary apparatus, the first light source 106 and the second light source 108 may form a light source assembly. It is noted that any number of light sources may be used. For example, in exemplary apparatus, three, four, five or more light sources may be used. Each light source may be configured to emit light at a different emission wavelength or range of wavelengths when compared to the other light sources. Alternatively, the emission wavelengths or range of wavelengths of one or more light sources may be coincident or overlap. Also, the plurality of light sources may be provided by a single tunable light source configured to emit light at one or more of a plurality of wavelengths or ranges of wavelengths. For example, the first and second light sources 106, 108 may be provided by a single tunable laser.

Similarly, the sensors may form part of a sensing assembly. In such apparatus, the sensing assembly may comprise any number of sensors. Typically, a separate sensor corresponds to each separate light source. In such apparatus, a sensor is configured to sense light received from the measurement location 102 as a result of the corresponding light source illuminating a cut gemstone located at the measurement location 102. However, in other exemplary apparatus, one sensor may correspond to a plurality of light sources. In such apparatus, a sensor may be configured to sense light received from the measurement location 102 as a result of a first corresponding light source illuminating a cut gemstone located at the measurement location 102 and also configured to sense light received from the measurement location 102 as a result of a second corresponding light source illuminating a cut gemstone located at the measurement location 102.

In the exemplary apparatus 100 of FIG. 1a, the measurements are made using two individual light sources 106, 108 and two corresponding individual spectrometers 110, 112 each coupled to a common fibre optic assembly 114. One or more optical filters may be included in the apparatus 100 to control the light entering each spectrometer 110, 112. Also, one or both of the light sources 106, 108 may comprise a shutter configured to selectively emit light from the light source 106, 108 into the corresponding fibre optic filament 114a, 114b. This may be beneficial if a light source 106, 108 cannot be switched on and off easily and/or quickly. The use of a shutter may also be beneficial when it is not technically possible to fabricate the ideal filter for controlling the light entering the spectrometer 110, 112 or fabrication costs are prohibitively high.

Figure 1B:
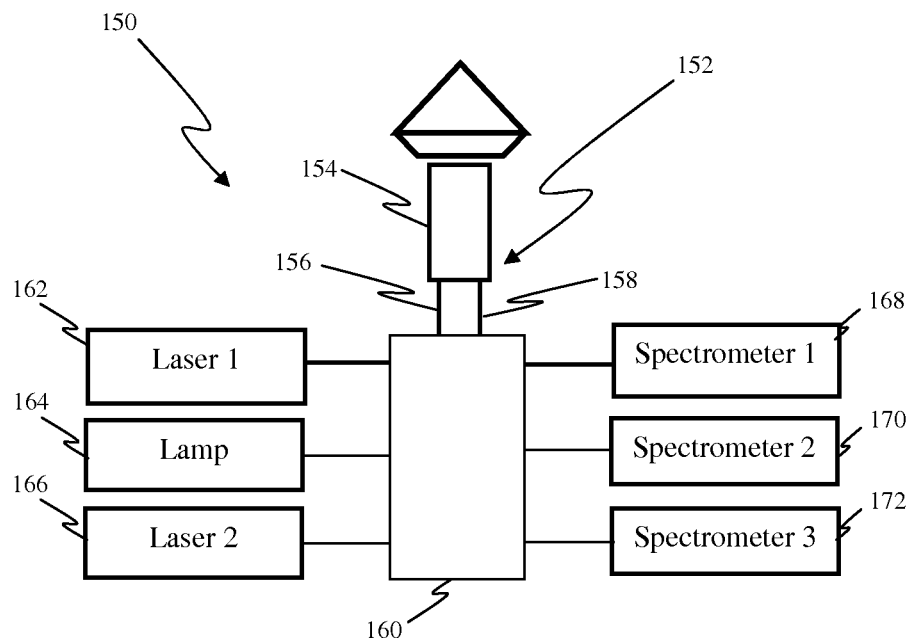
FIG. 1b shows a schematic representation of an apparatus for measuring a plurality of parameters of a cut gemstone.

FIG. 1b shows a schematic representation of another apparatus 150. The apparatus 150 has a different configuration to the apparatus 100 and uses a bi-furcated fibre optic assembly and optical multiplexer/demultiplexer. Many of the features of the apparatus 150 are similar to those of the apparatus 100 and are therefore not discussed again in detail. Description of the apparatus 150 is therefore limited to those features that are different to those of apparatus 100.

The apparatus 150 comprises an optical fibre assembly 152 comprising a bi-furcated fibre optic cable 154. The fibre optic cable 154 comprises first and second filaments 156, 158. The fibre optic cable 154 is in optical communication with an optical multiplexer/demultiplexer 160. The optical multiplexer/demultiplexer 160 is configured to receive a plurality of optical signals and to output one or more of the plurality of optical signals. The optical multiplexer/demultiplexer 160 is further configured to receive a single optical signal and to output the optical signal on one of a plurality of outputs.

A plurality of light sources 162, 164, 166 is in optical communication with the optical multiplexer/demultiplexer 160. A plurality of spectrometers 168, 170, 172 is in optical communication with the optical multiplexer/demultiplexer 160.

In exemplary apparatus 150, the optical multiplexer/demultiplexer 160 is configured to select one of the inputs from one of the plurality of light sources 162, 164, 166 and output the selected light source signal on the first filament 156 of the optical cable 154. In exemplary apparatus 150, the optical multiplexer/demultiplexer 160 is configured to select one of the plurality of spectrometers 168, 170, 172 and to output the optical signal received on the second filament 158 to the selected spectrometer.

It is noted that optical multiplexer/demultiplexers having a number of configurations may be used. For example, the MPM-2000 optical multiplexer is a product sold by Ocean Optics. Two versions are sold: a first version has 1 input and 16 outputs and a second version has 2 inputs and 8 outputs per input. The second version (with 2 inputs and 8 outputs) may be used in the apparatus 150. The 2 inputs may be attached to the first and second filaments 156, 158 of the bifurcated fibre 152 and there would then be provision for up to 8 different spectrometers and up to 8 different light sources.

A benefit of this arrangement is that only a bifurcated fibre is needed at the measurement location. A disadvantage may be that there is up to a 50% loss in light because there is a need to couple to one of the 8 inputs/outputs. The switching between inputs/outputs may be done by a motor and can be computer controlled.

Figure 2A:
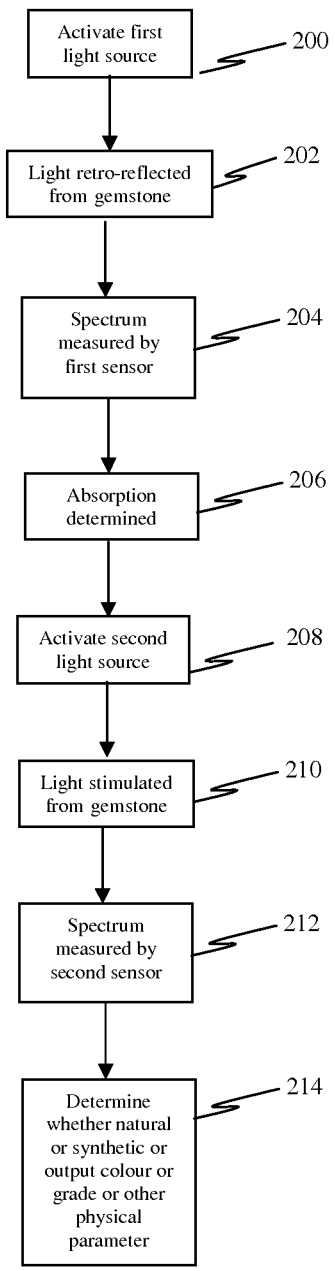
FIG. 2a is a flow chart showing a method of measuring a plurality of parameters of a cut gemstone.

FIG. 2a shows a flow diagram of a method for measuring a plurality of parameters of a cut gemstone.

The first light source 106 is activated 200 to emit light into the optical filament 114a of the optical fibre assembly 114. The optical fibre assembly 114 directs the emitted light to a cut gemstone 104 located at the measurement location 102. The broadband light emitted by the first light source 106 illuminates the gemstone 104. The emitted light is retro-reflected 202 by the gemstone 104. The reflected light enters the optical fibre assembly 114 and is directed to the first sensor 110 along the filament 114c. The first sensor 110 measures 204 the spectrum of the reflected light for determining the absorption of the gemstone 104. The absorption of the gemstone 104 may be determined 206 by the first sensor 110 or by the processor 118.

The second light source 108 is activated 208 to emit light at a wavelength of 660 nm into the filament 114b of the fibre optic assembly 114. The filament 114b directs the emitted light to the gemstone 104 positioned at the measurement location 102, which stimulates Raman emission 210 from the gemstone 104. The light emitted from the gemstone 104 enters the filament 114d of the optical fibre assembly 114 and is directed to the second sensor 112. The second sensor 112 measures the spectrum of Raman scattered light or other photoluminescent emission 212. The Raman spectrum measurement may be carried out at room temperature.

Following the determination of the absorption and Raman spectrum and or photoluminescent features of the gemstone 104, the processor 118 determines whether the gemstone is natural or synthetic. The apparatus may further determine a colour, grade or other physical parameter of the gemstone. The apparatus may be configured to sort the gemstone 104 based on the determination of whether it is natural or synthetic.

Previously known apparatuses carry out an absorption measurement and gemstones are then dispensed into separate bins depending on the result. The bins may comprise "pass", "pass-check with thermal pen", "refer (type II)" and "refer". The inventors have appreciated that, when screening melee, the number of stones receiving a "pass check with thermal pen" result can be around 20%. This means that around 20% of the stones have to undergo thermal pen testing to confirm whether they are natural diamond or simulant. The inventors have further appreciated that the incorporation of a Raman measurement removes the need for thermal pen testing. The Raman measurement can confirm whether the stone under test is diamond and if made alongside an absorption measurement, allows "pass check with thermal pen" results to be reclassified as "pass" or "non-diamond" results and therefore removes the need for a separate thermal pen test.

In order to further reduce measurement time the absorption measurement and the Raman measurement have been combined such that the stone does not have to move between measurements. The stone therefore remains at a single measurement location while the measurements are made.

In specific exemplary methods and apparatus, the absorption and Raman measurements may be made simultaneously. This is made possible because of careful selection of the first and second emission wavelengths or ranges of wavelengths and the first and second sensing wavelengths or ranges of wavelengths. In addition, a plurality of optical filters may be configured to select the wavelengths of light that reach each spectrometer. Also a lamp shutter and or filters may be required, as explained above.

Figure 2B:
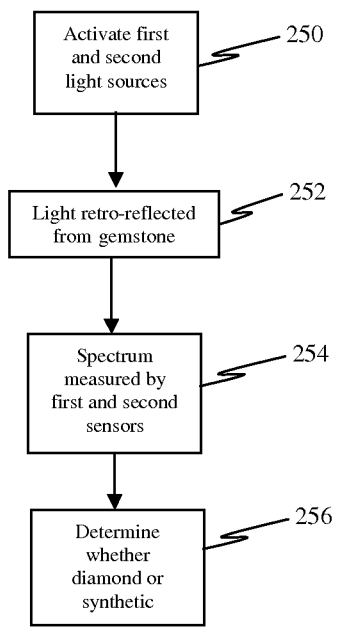
FIG. 2b is a flow chart showing a method of measuring a plurality of parameters of a cut gemstone.

FIG. 2b shows a flow diagram of a method for simultaneously measuring a plurality of parameters of a cut gemstone. First and second light sources are activated 250 such that they are emitting light simultaneously. The light emitted by each light source is reflected 252 from a gemstone positioned at a measurement location. The reflected light is directed to first and second spectrometers where it is measured 254. The measured spectrums are used to determine 256 whether the gemstone is diamond or synthetic.

In such methods, the absorption measurement may be made over the wavelength range 300 nm to 520 nm whereas the laser excitation for the Raman may be at 660 nm and the Raman and or photoluminescence measurement range may be 700 nm to 800 nm. Therefore, the first light source emits light in the wavelength range 300 nm to 520 nm, whereas the second light source (for the Raman and or photoluminescence measurement) emits light at a wavelength of 660 nm Selecting two different wavelength ranges for each measurement avoids interference between each system and allows simultaneous operation, thereby saving total measurement time. In addition, optical filters may be used to control the wavelength range of the light sources and control the wavelength range of the light entering the sensors. Further, the quad-furcated fibre optic assembly 114 allows light to travel from each of the light sources and to each of the sensors without interference. However, in certain circumstances it may be beneficial to obtain the measurements sequentially. Provision to shutter a lamp may be required if, for example, the lamp has a relatively long warm-up time. Provision to shutter a lamp may also be required when it is not technically possible to fabricate the ideal filters for controlling the wavelength range emitted by the light sources or collected by the sensors, or fabrication costs are prohibitively high.

The apparatus and methods disclosed herein may provide simultaneous measurement of a plurality of parameters of a cut gemstone and/or sequential measurement of a plurality of parameters of a cut gemstone while it remains in the same position. The gemstone under test may, for example, be placed on a fibre optic measurement probe or, to provide another example, the stone could be placed on a disc and light focussed onto the gemstone and then collected for analysis. The light may be focussed on the gemstone either from above or below. In embodiments in which the light is focussed from below, the disc may be transparent.

The methods disclosed with respect to FIGS. 2a and 2b may be automated. That is, the apparatus disclosed herein may be configured to determine that a gemstone is present at the measurement location and, dependent on that determination, to emit light from one or more light sources to the measurement location. One or more spectrometers are then configured to receive light from the gemstone and determine spectral data. A processor may be configured to acquire and read the spectral data from the spectrometers, process the spectral data and output a result/decision. This process may be automated or semi-automated and may be computer or instrument controlled.

Figure 3:
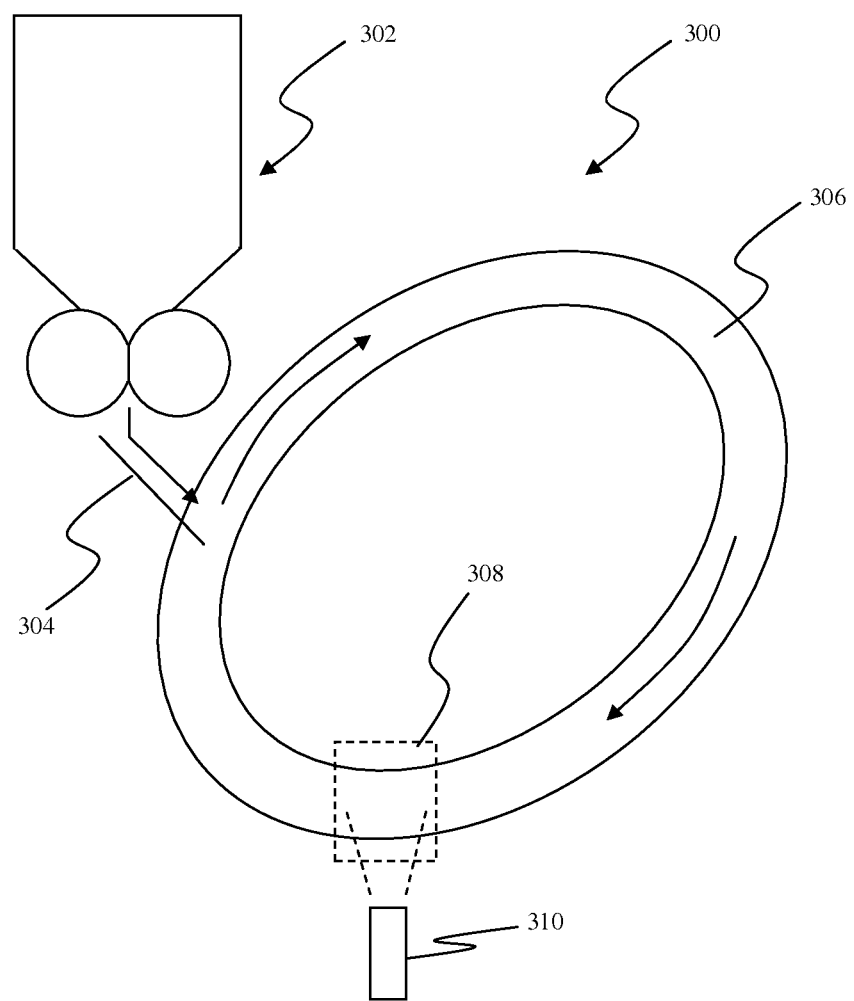
FIG. 3 shows a schematic representation of an apparatus for measuring a plurality of parameters of a cut gemstone.

FIG. 3 shows a simplified schematic view of a device 300 for measuring a parameter of a particle of particulate material. A feeder 302 and a slope 304 are configured to direct stones onto the rotating disc 306. A measurement location 308 is located at a point on a path followed by a stone as the disc 306 is rotated. An apparatus 310 for measuring a plurality of parameters of a cut gemstone, as described above, is located proximal to the measurement location 308 and is configured to measure a plurality of parameters of a stone located at the measurement location 308. In exemplary devices, the apparatus 310 is located above the measurement location 308. That is, when a stone is at the measurement location 308, the apparatus 310 is on an opposite side of the stone to the disc 306. In embodiments in which the disc 306 is transparent, the apparatus 310 may be located beneath the disc 306 and may measure parameters through the disc 306.

The device 300 is configured such that the disc 306 rotates to transport the stones from the feeder 302 to the measurement location 308. The device 300 is further configured such that the disc 306 stops rotating when the stone has reached the measurement location 308. In this way, the stone may be held at the measurement location 308 for a sufficient period of time to allow more accurate measurements to be taken.

Multiple measurements are made while the gemstone is in the same measurement location. Measurements may be made simultaneously and/or sequentially. The measurements may comprise one or more of: absorption, Raman, Photoluminescence and image based measurements. The image based measurements could be configured to give size and cut information.

Figure 4:
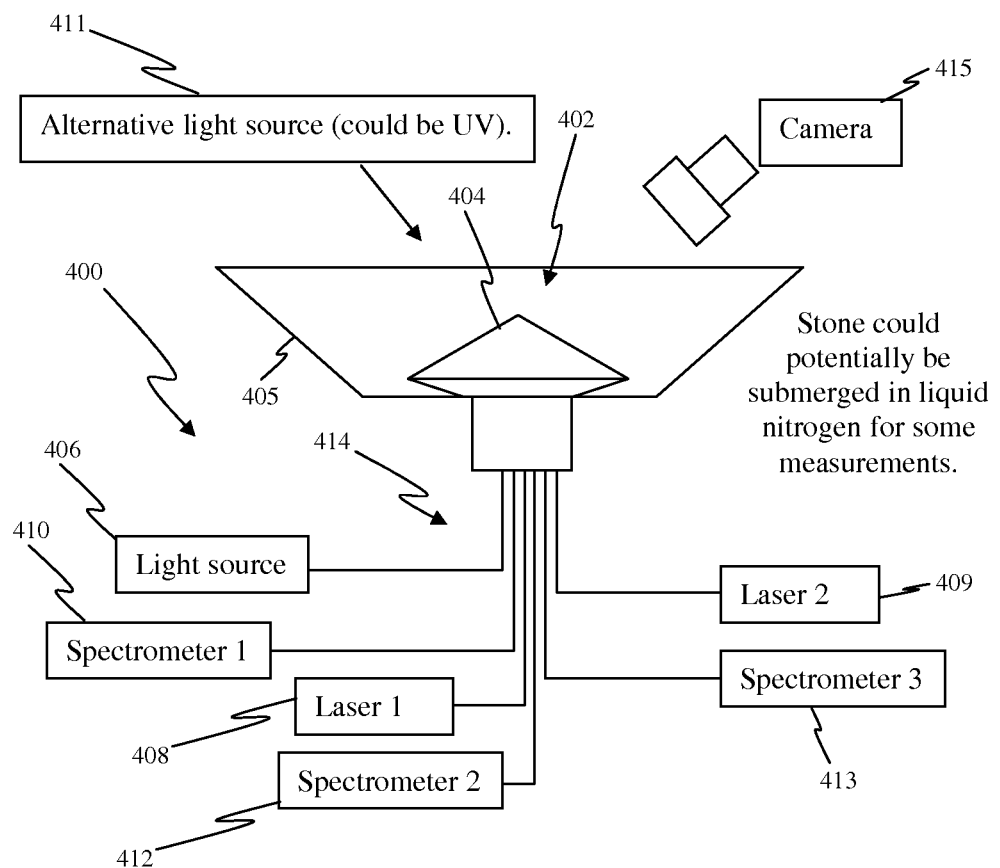
FIG. 4 shows a schematic representation of an apparatus for measuring a plurality of parameters of a cut gemstone.

FIG. 4 shows an apparatus 400 for measuring a plurality of parameters of a cut gemstone. The apparatus defines a measurement location 402 and is configured to cause or allow a cut gemstone 404 to be positioned at the measurement location 402. The measurement location 402 is positioned within a receptacle 405. The receptacle may be filled with a cold fluid, such as liquid nitrogen.

The apparatus 400 comprises a first light source 406, which is similar to the first light source 106 of FIG. 1a and is therefore not described here. The apparatus 400 comprises a second light source 408, which is similar to the second light source 108 of FIG. 1a and is therefore not described here. In addition, the apparatus 400 comprises a third light source 409. The third light source 409 is a laser device configured to emit light for measuring the photoluminescence of the cut gemstone 404. The third light source may be configured to emit light substantially at wavelengths of one or more of 325 nm, 375 nm, 458 nm, 514 nm, 785 nm and 830 nm. In other exemplary apparatus, the third light source may comprise a plurality of light sources, each configured to emit light substantially at a wavelength of one of 325 nm, 375 nm, 458 nm, 514 nm, 785 nm and 830 nm. The apparatus 400 also comprises a fourth light source 411. The fourth light source is configured to emit light for measuring the fluorescence and or phosphorescence of the cut gemstone 404. In the exemplary apparatus 400, the fourth light source emits light in the UV spectrum.

In exemplary apparatus, one or more of the light sources, for example the third light source, may be a broad band light source, such as a Tungsten halogen lamp. In exemplary apparatus, one or more light sources may be configured selectively to emit either laser light or broadband light. For example, an LED may be mounted on a moving arm within a casing of a light source and, when the LED is moved into a position at which broad band or laser light is emitted from the casing, the moving arm blocks emission of light from the broad band or laser light source.

The apparatus 400 comprises a first sensor 410, which is similar to the first sensor 110 in FIG. 1a and is therefore not described in detail here. The first sensor 410 corresponds to the first light source 406 in that it is configured to receive light from the measurement location 402 as a result of the gemstone 404 being illuminated by the first light source 406. The first light source 406 and the first sensor 410 are configured to undertake an absorption measurement of the gemstone 404. The apparatus 400 comprises a second sensor 412, which is similar to the second sensor 112 in FIG. 1a and is therefore not described in detail here. The second sensor 412 corresponds to the second light source 408 in that it is configured to receive light from the measurement location 402 as a result of the gemstone 404 being illuminated by the second light source 408. The second light source 408 and the second sensor 412 are configured to undertake a Raman measurement of the gemstone 404. In particular embodiments, a third light source and a third sensor could also emit and detect broad band illumination, thus making an absorption measurement.

The apparatus 400 also comprises a third sensor 413. The third sensor 413 comprises a spectrometer configured to sense light emitted by photoluminescence from the gemstone 404. Specifically, the third sensor 413 is configured to sense light substantially at one or more of a range from 380 nm to 520 nm and a range from 460 nm to 850 nm. In other exemplary apparatus, the third sensor may comprise a plurality of sensors, each configured to sense light substantially in the range from 380 nm to 520 nm or the range from 460 nm to 850 nm. The third sensor 413 corresponds to the third light source 409 in that it is configured to receive light from the measurement location 402 as a result of the gemstone 404 being illuminated by the third light source 409. The third light source 409 and the third sensor 413 are configured to undertake a photoluminescence measurement of the gemstone 404.

The apparatus 400 also comprises a fourth sensor 415. The fourth sensor 415 is a camera or PMT sensor configured to sense light for emitted by fluorescence or phosphorescence from the gemstone 404. Specifically, the camera is configured to sense light in the range from 400 nm to 700 nm. The camera may be configured to sense visible light. The fourth sensor 415 corresponds to the fourth light source 411 in that it is configured to receive light from the measurement location 402 as a result of the gemstone 404 being illuminated by the fourth light source 411. The fourth light source 411 and the fourth sensor 415 are configured to undertake a fluorescence or phosphorescence measurement of the gemstone 404.

The light sources 406, 408, 409 and sensors 410, 412, 413 are optically coupled to an optical fibre assembly in a similar way to that described above in relation to the apparatus 100 of FIG. 1a. The fourth light source 411 is arranged to emit light directly onto the gemstone 404. The fourth sensor 415 is configured to detect directly light from the gemstone 404.

The apparatus may also comprise a processor similar to the processor 118 shown in FIG. 1a.

It is noted that the apparatus 100 of FIG. 1a may comprise one or more of the light sources and sensors of the apparatus 400 of FIG. 4 in addition to or as an alternative to the light sources and sensors shown in FIG. 1a.

Each feature disclosed or illustrated in the present specification may be incorporated in the apparatus or methods disclosed herein, whether alone or in any appropriate combination with any other feature disclosed or illustrated herein.

The apparatus 400 is operated in a similar fashion to the apparatus 100 and as disclosed in FIG. 2. Each corresponding pair of light source and sensor is operated to carry out a measurement of a parameter of the gemstone 404 while it is at the measurement location 402.

Using the apparatus 400, two or more of the absorption measurement, the Raman measurement and the photoluminescence measurement may be carried out simultaneously. Specifically, the absorption measurement and the Raman measurement may be carried out simultaneously. Further, the Raman measurement and the photoluminescence measurement may be carried out simultaneously. The absorption measurement and the photoluminescence measurement may be carried out sequentially. Sequential absorption and photoluminescence measurements may be required when it is not technically possible to fabricate ideal optical filters for controlling the wavelength range emitted by the light sources or collected by the sensors, or fabrication costs are prohibitively high.

As mentioned above, current apparatus such as De Beer's AMS apparatus, make an absorption measurement, for example, using light having a wavelength in a range from 300 nm to 508 nm and a separate photoluminescence measurement, for example, using light having a wavelength in a range from 700 nm to 800 nm. Following these separate measurements, a stone may be dispensed to one of five bins depending on both measurement results. Stones deposited in a 'PASS' bin require no further testing after measurement, whereas stones deposited in a 'REFER TYPE II' bin require further testing.

Further testing typically involves removing stones from the apparatus and conducting photoluminescence measurements with another apparatus. The inventors have appreciated that it would be advantageous to make these additional measurements within a single apparatus as the overall pass rate of the apparatus would be improved and the movement of stones to another instrument would be avoided. Also, the additional cost of another screening instrument would not be incurred.

In order to reduce cost and complexity methods and apparatus have been developed which utilise a single spectrometer and a relatively inexpensive UV LED light source.

Figure 5:
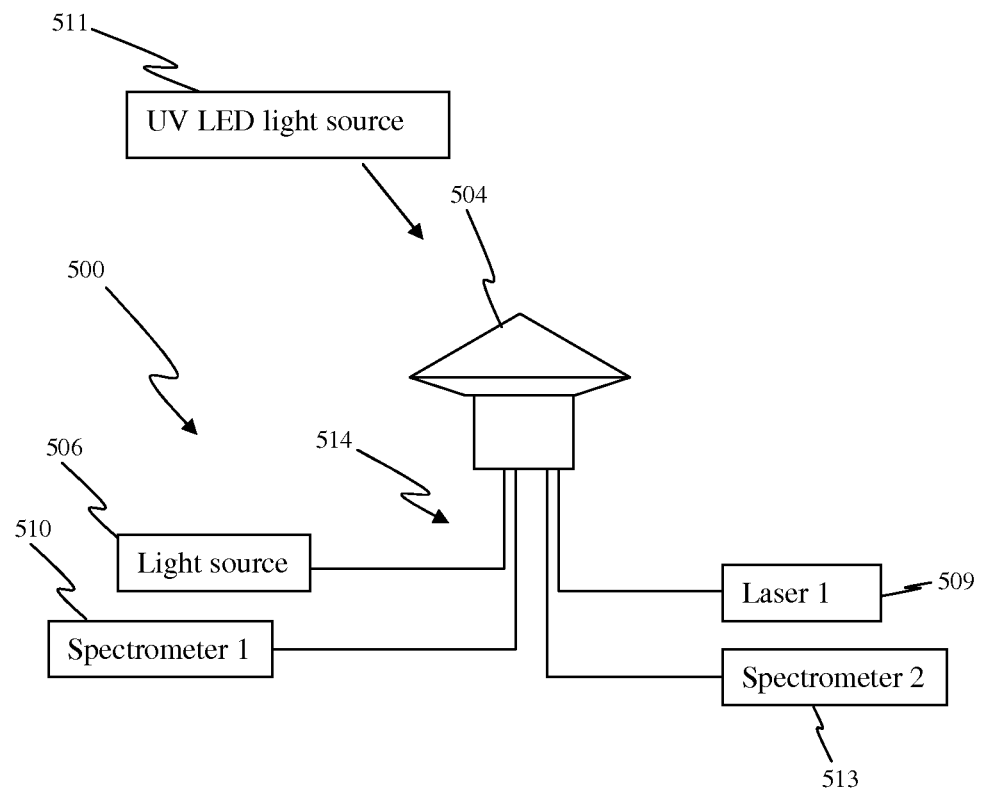
FIG. 5 shows a schematic representation of an apparatus for measuring a plurality of parameters of a cut gemstone.

FIG. 5 shows a schematic diagram of an apparatus 500 comprising a UV LED 511. The apparatus of FIG. 5 has the ability to make absorption, photoluminescence and fluorescence measurements on a polished diamond.

A first light source 506 and first spectrometer 510 are used to make an absorption measurement. The UV LED light source 511 and the first spectrometer 510 are used to make the fluorescence measurement and the laser 509 and the second spectrometer 513 are used to make a Raman/photoluminescence measurement. It is noted that the inclusion of the laser 509 and the second spectrometer 513 are optional.

The apparatus in FIG. 5 does not require an additional spectrometer to measure absorption and fluorescence as the first spectrometer 510 is used for both. Additional fibre optic cables are also not required because the excitation illumination is introduced overhead by the UV LED light source 511 rather than being delivered through a fibre optic cable. The UV LED light source 511 is used rather than a more costly laser light source.

In exemplary methods and apparatus, the first spectrometer 510 may utilise a charge coupled device (CCD) detector. In specific exemplary methods and apparatus, the first spectrometer 510 may be a 'miniature' spectrometer comprising a CCD detector. In such devices, the light is incident upon a slit then dispersed from a reflective diffraction grating onto a long CCD detector (typically 2048×14 pixels).

Figure 6:
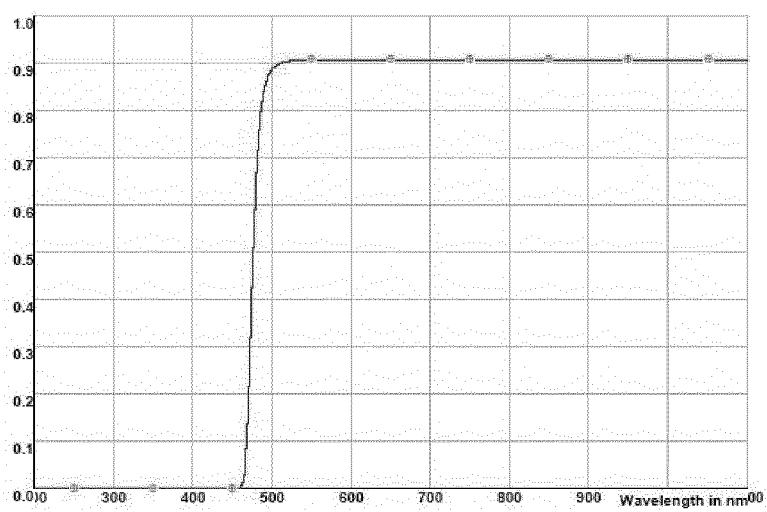
FIG. 6 shows a transmission spectrum for a typical long pass filter.

Typically, in known solutions, photoluminescence and fluorescence measurements are made with separate dedicated spectrometers and the excitation light is prevented from entering the spectrometer by the use of a long wavelength pass filter (long pass filter). The long pass filter is typically fitted behind the entrance slit of the spectrometer and rejects light below a defined wavelength. For example, if the excitation wavelength is 365 nm the long pass filter will generally transmit light at 390 nm and above. FIG. 6 gives a transmission spectrum for a typical long pass filter.

Without the long pass filter present, the excitation light would enter the spectrometer and cause saturation of the CCD detector preventing the fluorescence or photoluminescence being detected. The fluorescence or photoluminescence intensity is generally much less than the incident excitation light intensity and therefore very difficult to detect even if the CCD detector is not in saturation.

A disadvantage of using a long pass filter is that no light can be detected by the spectrometer at wavelengths within the long pass filter rejection band. Therefore, absorption measurements in this region are not possible.

One solution is to have a long pass filter which is mechanically removable, but this increases complexity and would mean a modification to the spectrometer body. A long pass filter could be added in the optical fibre line and be mechanically removable, but breaking this line and recombining after the filter generally results in a loss of light of approximately 40%.

Methods and apparatus disclosed herein allow absorption measurements in a range from 300 nm to 508 nm and fluorescence measurements in a range from 400 nm to 508 nm using the same spectrometer without the need for a long pass filter.

Figure 7:
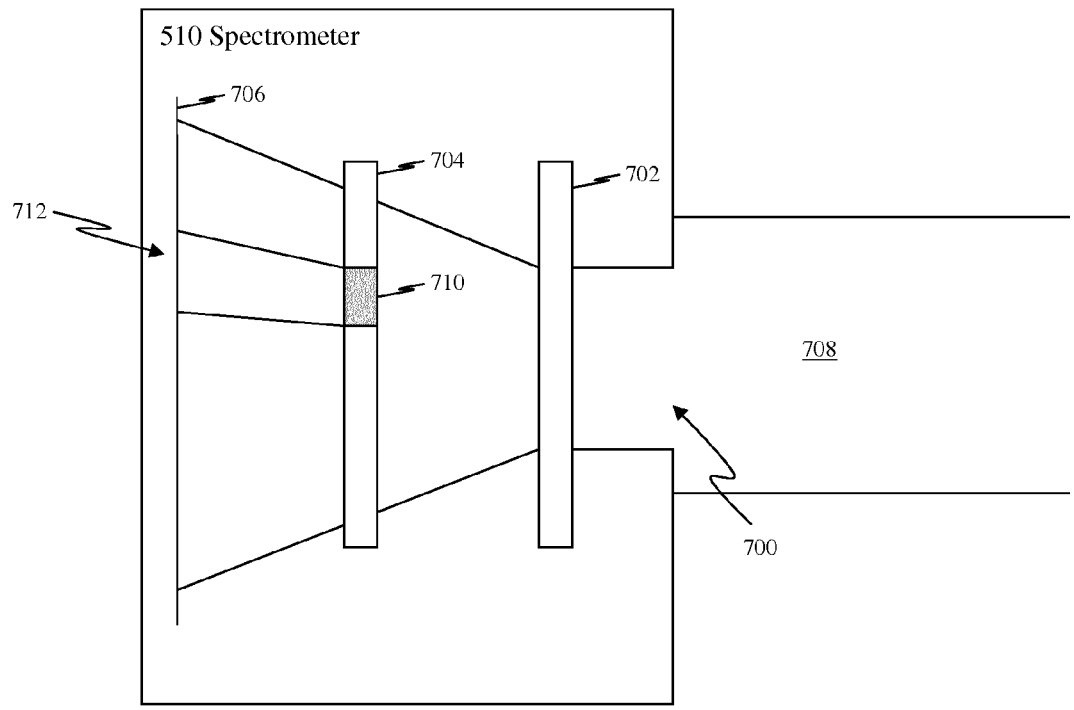
FIGS. 7 and 8 show a schematic representations of a spectrometer comprising a mask.

Referring to FIG. 7, a schematic of the first spectrometer 510 is shown. The spectrometer 510 comprises a slit 700, a diffraction grating 702, a mask 704 and a CCD array 708. A light beam 708 is incident on the slit 700 and light passes through the slit and is dispersed by the diffraction grating 702. The dispersed light is then incident on the CCD array 706 via the mask 704. The mask comprises a masking region 710 which corresponds to light having wavelengths in the range from 350 nm to 400 nm such that that light is blocked and does not reach the CCD array 706, which is shown by the area 712 on the CCD array 706. The mask blocks all light incident onto the spectrometer's CCD detector in a particular wavelength range, which in exemplary methods and apparatus includes the UV LED light at 365 nm. Therefore, fluorescence spectra from 400 nm to 508 nm can be measured without the CCD detector being saturated. The diffraction grating shown in FIG. 7 is a transmission grating, but a reflection grating can also be used.

Absorption measurements can also be made from 300 nm to 350 nm and 400 nm to 508 nm. The information contained within the masked 350 nm to 400 nm region is not relevant to screening diamond and is not used to determine if a diamond is natural or synthetic.

The application of a mask to the first spectrometer CCD detector 706 allows the spectrometer to be used for both fluorescence and absorption measurements on diamond.

Figure 8:
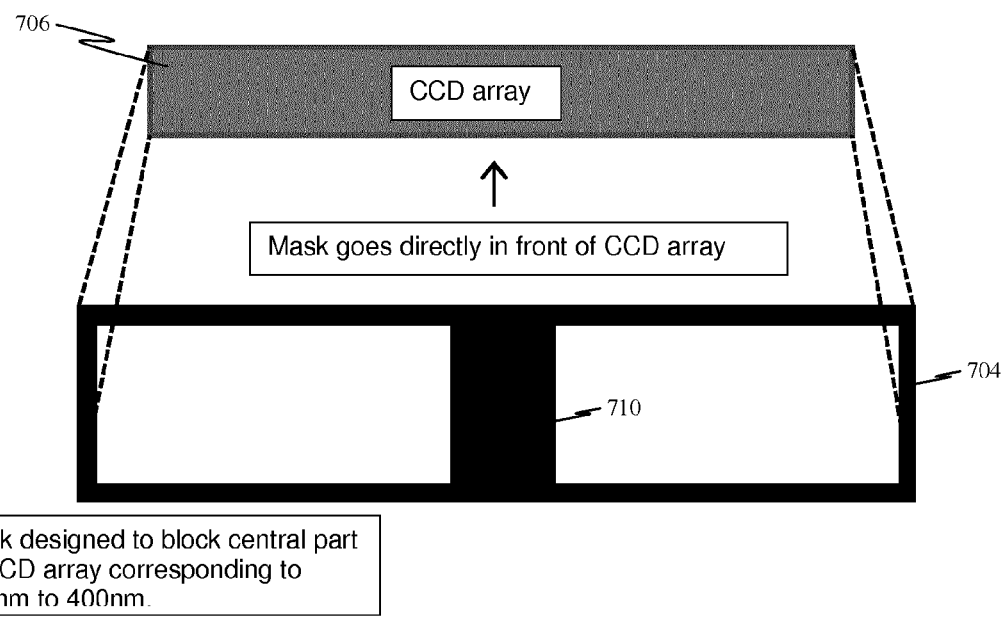

FIG. 8 shows an isometric representation of the mask 704 and the CCD array 706. The masking region 706 can be seen and is configured to block light. Either side of the masking region 710 are openings through which light may pass.

The fluorescence measurement may be carried out sequentially with any other measurement.

A computer program may be configured to provide any of the above described methods. The computer program may be provided on a computer readable medium. The computer program may be a computer program product. The product may comprise a non-transitory computer usable storage medium. The computer program product may have computer-readable program code embodied in the medium configured to perform the method. The computer program product may be configured to cause at least one processor to perform some or all of the method.

Various methods and apparatus are described herein with reference to block diagrams or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

Computer program instructions may also be stored in a computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-ray).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and/or flowchart block or blocks.

Accordingly, the invention may be embodied in hardware and/or in software (including firmware, resident software, micro-code, etc.) that runs on a processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated.

The skilled person will be able to envisage other embodiments without departing from the scope of the appended claims.

The invention claimed is:

1. An apparatus for measuring a plurality of parameters of a cut gemstone while it is positioned at a single measurement location, the apparatus comprising:
   a plurality of light sources each configured to emit light at a different one of a plurality of emission wavelengths or ranges of wavelengths such that the emitted light illuminates at least part of the measurement location;
   a sensor assembly configured to sense light at a plurality of sensing wavelengths or ranges of wavelengths for measuring the plurality of parameters, the sensed light being received at the sensor assembly from the measurement location as a result of illumination of a cut gemstone located at the measurement location, wherein the sensor assembly comprises a plurality of sensors, each configured to sense light at a different one or more of the plurality of sensing wavelengths or ranges of wavelengths; and
   a multi-furcated optical fibre assembly configured to direct light from the light source assembly to the measurement location and to direct light from the measurement location to the sensor assembly, the multi-furcated optical fibre assembly comprising a plurality of optical fibre filaments, each configured to direct light from one of the plurality of light sources to one of the plurality of sensors;
   wherein the plurality of light sources includes a broadband light source configured to emit light for measuring the absorption of a cut gemstone, and a laser light source configured to emit light at a wavelength suitable for stimulating Raman emission at a detectable wavelength from a cut gemstone;
   and wherein the plurality of sensors includes a first spectrometer configured to sense light at a range of wavelengths for measuring the absorption of a cut gemstone, and a second spectrometer configured to sense light at a range of wavelengths for measuring the Raman emission spectrum of a cut gemstone.

2. An apparatus according to claim 1, wherein the broadband light source is configured to emit light at wavelengths in the range from about 300 nm to about 520 nm.

3. An apparatus according to claim 1, wherein the laser light source is configured to emit light at about 660 nm.

4. An apparatus according to claim 1, wherein the plurality of light sources comprises at least one laser light source configured to emit light at a wavelength suitable for stimulating photoluminescence in a cut gemstone.

5. An apparatus according to claim 4, wherein the at least one laser light source configured to emit light at a wavelength for stimulating photoluminescence in a cut gemstone comprises at least one laser light source configured to emit light substantially at a wavelength of one of about 325 nm, about 375 nm, about 458 nm, about 514 nm, about 785 nm and about 830 nm.

6. An apparatus according to claim 1, wherein the first or second spectrometer comprises a wavelength restriction means configured to prevent detection of light in a certain wavelength range.

7. An apparatus according to claim 6, wherein the spectrometer comprises a charge coupled device and wherein the wavelength restriction means comprises a mask located before the charge coupled device on a path of light entering the spectrometer.

8. An apparatus according to claim 7, wherein the spectrometer further comprises a diffraction grating located before the mask on the path of light entering the spectrometer.

9. An apparatus according to claim 6, wherein the wavelength range is from 350 nm to 400 nm.

10. An apparatus according to claim 1, further comprising a UV light source configured to emit light for measuring fluorescence of the cut gemstone,
    and wherein the spectrometer is configured to measure fluorescence in a wavelength range from 400 nm to 508 nm and to measure absorption in two ranges from 300 nm to 350 nm and from 400 nm to 508 nm.

11. An apparatus according to claim 10, configured to measure fluorescence and absorption of the cut gemstone simultaneously.

12. An apparatus according to claim 1, wherein the first spectrometer is configured to sense light at a wavelength range from about 300 nm to about 520 nm.

13. An apparatus according to claim 1, wherein the second spectrometer is configured to sense light at a wavelength range from 700 nm to 800 nm.

14. An apparatus according to claim 1, wherein the plurality of sensors comprises at least one additional spectrometer configured to sense light at a wavelength for measuring the photoluminescence of a cut gemstone.

15. An apparatus according to claim 14, wherein the at least one additional spectrometer is configured to sense light at a wavelength in at least one of a range from about 380 nm to about 520 nm; and a range from about 460 nm to about 850 nm.

16. An apparatus according to claim 1, wherein the plurality of sensors comprises an image capturing device configured to sense light at a wavelength for measuring the fluorescence or phosphorescence of a cut gemstone.

17. An apparatus according to claim 16, wherein the image capturing device is a camera configured to sense light at a wavelength range from about 400 nm to about 700 nm.

18. An apparatus according to claim 17, wherein the image capturing device is configured to capture an image for determining the cut of a gemstone and/or the size of a gemstone.

19. An apparatus according to claim 1, comprising an optical multiplexer comprising a plurality of inputs each connected to a different one of the plurality of light sources, and an output for directing light to the measurement location, the optical multiplexer configured to select light received at one of the plurality of inputs and allow the selected light to be emitted from the output.

20. An apparatus according to claim 1, comprising an optical demultiplexer comprising an input configured to receive light from the measurement location, and a plurality of outputs each connected one of the plurality of sensors, the optical demultiplexer configured to select one of the plurality of outputs and to allow light received at the input to be emitted from the selected output.

21. An apparatus according to claim 1, further comprising means for determining whether a cut gemstone is natural or synthetic based on the measured parameters.

22. An apparatus according to claim 21, further comprising a means of distinguishing between diamond and simulant.

23. An apparatus according to claim 1, further comprising means for determining whether a cut gemstone has been treated in order to improve its colour based on the measured parameters.

24. An apparatus according to claim 1, configured to measure simultaneously the absorption of a cut gemstone and the Raman emission spectrum of a cut gemstone.

25. An apparatus according to claim 1, configured to measure simultaneously the photoluminescence of a cut gemstone and the Raman emission spectrum of a cut gemstone.

26. A sorting apparatus comprising the apparatus of claim 1, and configured to sort cut gemstones in dependence on the measured parameters.

27. A sorting apparatus according to claim 26, wherein sorting the cut gemstones comprises identifying whether the gemstone has been treated to improve its colour.

28. A sorting apparatus according to claim 26, wherein sorting the cut gemstones comprises determining one or more of the colour, size and cut of the gemstone.

29. A sorting apparatus according to claim 26, wherein sorting the cut gemstones comprises distinguishing between diamonds and simulants.

30. The apparatus of claim 1, wherein the first or second spectrometer comprises a wavelength restriction means configured to prevent detection of light in a certain band of wavelengths.

31. An apparatus according to claim 30, wherein the first or second spectrometer comprises a charge coupled device and wherein the wavelength restriction means comprises a mask located before the charge coupled device on a path of light entering the spectrometer.

32. An apparatus according to claim 31, wherein the first or second spectrometer further comprises a diffraction grating located before the mask on the path of light entering the spectrometer.

33. A method for measuring a plurality of parameters of a cut gemstone while it is positioned at a single measurement location, the method comprising:
operating a broadband light source to illuminate at least part of the cut gemstone with light having a first emission range of wavelengths configured for measuring the absorption of the cut gemstone;
operating a first spectrometer to sense light received from the measurement location at a first sensing range of wavelengths as a result of illumination of the cut gemstone at the first emission range of wavelengths;
measuring an absorption of the cut gemstone based on the sensed light at the first sensing range of wavelengths;
operating a laser light source to illuminate at least part of the cut gemstone with light having a second emission wavelength or range of wavelengths different to the first emission range of wavelengths and configured to stimulate Raman emission at a detectable wavelength from the cut gemstone;
operating a second spectrometer to sense light received from the measurement location at a second sensing wavelength or range of wavelengths as a result of illumination of the cut gemstone at the second emission wavelength or range of wavelengths; and
measuring a Raman emission of the cut gemstone based on the sensed light at the second sensing wavelength or range of wavelengths;
wherein light is directed from the broadband light source and the laser light source to the measurement location and from the measurement location to the first and second spectrometers using a multi-furcated optical fibre assembly.

34. A method according to claim 33, wherein the first sensing range of wavelengths is different to the second sensing wavelength or range of wavelengths.

35. A method according to claim 33, wherein each of the broadband light source and laser light sources is operated such that they emit light simultaneously.

36. A method for sorting cut gemstones comprising the method of claim 33 and further comprising sorting the cut gemstones in dependence on the measured parameters.

37. A non-transitory computer program product configured to carry out the method of claim 33.

* * * * *